United States Patent [19]

Strecker

[11] 4,338,442
[45] Jul. 6, 1982

[54] PREPARATION OF 1,5-METHYLENE-3,7-DINITRO-1,3,5,7-TETRAAZACYCLOOCTANE

[75] Inventor: Richard A. Strecker, Randolph, N.J.

[73] Assignee: The United States of America as represented by the Secretary of the Army, Washington, D.C.

[21] Appl. No.: 254,567

[22] Filed: Apr. 15, 1981

[51] Int. Cl.$^3$ .................................... C07D 251/72
[52] U.S. Cl. ................................................ 544/215
[58] Field of Search .................. 544/186, 215, 180; 260/239 H, 239 M

[56] References Cited

U.S. PATENT DOCUMENTS 2,678,927  5/1954  Wright et al. .................. 544/215
4,069,220  1/1978  Orem et al. .................... 544/186

Primary Examiner—Henry R. Jiles
Assistant Examiner—Robert C. Whittenbaugh
Attorney, Agent, or Firm—Nathan Edelberg; Robert P. Gibson; A. Victor Erkkila

[57] ABSTRACT 1,5-Methylene-3,7-dinitro-1,3,5,7-tetraazacyclooctane (DPT) is prepared by reacting nitrourea with formaldehyde in aqueous solution in the presence of sufficient added water soluble base, such as sodium hydroxide, to initiate evolution of carbon dioxide gas and formation of an intermediate compound, and reacting the intermediate compound with aqueous ammonia and formaldehyde to form DPT.

6 Claims, No Drawings

PREPARATION OF 1,5-METHYLENE-3,7-DINITRO-1,3,5,7-TETRAAZACYCLOOCTANE

GOVERNMENT RIGHTS

The invention described herein may be manufactured, used and licensed by the Government for Government purposes without the payment to me of any royalty thereon.

BACKGROUND OF THE INVENTION

This invention relates to a novel process for preparing 1,5-methylene-3,7-dinitro-1,3,5,7-tetraazacyclooctane, also known as dinitropentamethylenetetramine or briefly as DPT, which is an intermediate for producing HMX.

HMX, 1,3,5,7-tetranitro-1,3,5,7-tetraazacyclooctane, is a very powerful military explosive, but its use has been limited by its high cost and availability. Current methods for manufacturing HMX involve the nitrolysis of hexamine. It is known that HMX can be prepared from DPT, and indeed DPT has been identified as a key intermediate in the formation of HMX from the nitrolysis of hexamine, which is also known as the Bachmann process. (W. J. Chute, D. C. Downing, A. F. McKay, G. S. Myers and G. F. Wright, Can. J. Research, 27B, 218(1949); W. E. Bachmann, W. J. Horton, E. L. Jenner, N. W. MacNaughton and L. B. Scott, J. Am. Chem. Soc., 73, 2769(1951); and W. E. Bachmann and E. L. Jenner, J. Am. Chem, Soc., 73, 2773(1951)).

In view of the importance of DPT in the synthesis of HMX, a low cost method for producing this intermediate would provide a significant contribution toward reducing the cost of manufacturing HMX. In the past DPT has been prepared by various methods, viz.

(1) nitrolysis of hexamine using acetic anhydride and 99+% nitric acid in acetic acid solvent;
(2) reaction of hexamine dinitrate and acetic anhydride;
(3) reaction of hexamine dinitrate and 90% $H_2SO_4$ and neutralization with ammonia to pH 6.5;
(4) reaction of hexamine, 99+% nitric acid and ammonium nitrate, and neutralization with ammonia to pH 6.5;
(5) reaction of nitramide, formaldehyde and ammonia; and
(6) reaction of nitramide, formaldehyde and methylenediamine sulfate.

The reactants used in all of these methods are costly (e.g. acetic anhydride and hexamine), or are difficult to prepare and handle (e.g. nitramide), so that the synthesis of HMX from DPT is more costly than the current process for manufacturing HMX by nitrolysis of hexamine.

An object of this invention is to provide a more economical process for producing DPT by employing reactants which are less costly than those used in prior art methods.

SUMMARY AND DETAILED DESCRIPTION OF THE INVENTION

Previous studies have shown that DPT can be obtained in high yields by the condensation reaction between nitramide, formaldehyde and ammonia. However, the use of nitramide on a large scale process for manufacturing DPT is impractical in view of its hydrolytic instability and difficulty and cost of preparation.

I have found a novel and inexpensive process for producing DPT by utilizing nitrourea as starting material in place of nitramide. The novel process comprises reacting nitrourea with formaldehyde in aqueous medium at a pH of about 2 or higher, preferably between about 2 and 3, to cause evolution of carbon dioxide gas and formation of an intermediate compound, and reacting the intermediate compound with ammonia and formaldehyde to form DPT.

The nitrourea starting material can be obtained in high yields from urea nitrate, which in turn can be readily produced from low cost urea (Organic Syntheses, vol, 1, page 417).

The process of the present invention can be carried out by mixing the nitrourea with aqueous formaldehyde until the nitrourea is completely dissolved. In the first stage of the process, the relatively acidic solution thus obtained is adjusted to a pH of about 2 or more with a water soluble base, such as sodium hydroxide, potassium hydroxide, sodium acetate, and ammonium hydroxide to cause a reaction characterized by the evolution of carbon dioxide gas and the formation of an intermediate compound. Ammonia is also liberated but in the acid medium is converted to a soluble ammonium salt. The reaction mixture is stirred preferably with heating until the evolution of carbon dioxide has ceased. In the second stage of the process, the intermediate compound is reacted with ammonia and formaldehyde to form DPT. This can be readily accomplished by neutralizing the solution with ammonium hydroxide to about pH 6-7 in the presence of additional formaldehyde if necessary, whereby the DPT is formed and precipitates from the solution.

Although not exactly known, it is believed that in the first stage of the process, the nitrourea reacts with the formaldehyde at the nitramide nitrogen to form N-methylol nitrourea, which undergoes hydrolysis with scission of the carbamido group and evolution of $CO_2$ and $NH_3$ and reaction with more formaldehyde causing the formation of an intermediate compound believed to be N-dimethylol nitramide. In the second stage of the process, the intermediate compound is reacted with ammonia and formaldehyde to form DPT. In the first reaction stage, two moles of formaldehyde are theoretically required per mole of nitrourea to form the intermediate compound believed to be N-dimethylol nitramide. In the second reaction stage, two moles of ammonia and one mole of formaldehyde are required to react with two moles of N-dimethylol nitramide (equivalent to two moles of nitrourea starting material) to form DPT according to the following reactions:

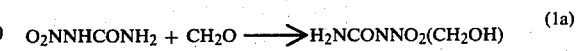
$$O_2NNHCONH_2 + CH_2O \longrightarrow H_2NCONNO_2(CH_2OH) \quad (1a)$$

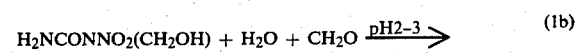
$$H_2NCONNO_2(CH_2OH) + H_2O + CH_2O \xrightarrow{pH2-3} \quad (1b)$$
$$O_2NN(CH_2OH)_2 + CO_2 + NH_3$$

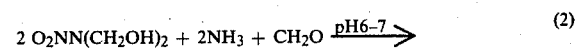
$$2\ O_2NN(CH_2OH)_2 + 2NH_3 + CH_2O \xrightarrow{pH6-7} \quad (2)$$

-continued

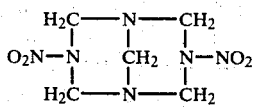

The use of larger amounts of formaldehyde and ammonia than those theoretically required is preferred, since it promotes the yield of DPT produced within limits. If desired, the total amount of formaldehyde required in the process may be present in the first reaction stage and thus be present to react with the the intermediate compound to form DPT in the second reaction stage.

In carrying out the first reaction stage of the present process, it is preferred to add sufficient base, e.g. sodium hydroxide, to bring the solution to about pH 2-3 to initiate and complete the evolution of carbon dioxide gas, and then neutralize the solution to about pH 6-7 with ammonium hydroxide in the presence of sufficient formaldehyde to form and precipitate the DPT. Substantially lower yields of DPT are obtained when the solution is neutralized to pH 6-7 in the first reaction stage and then mixed with ammonium hydroxide to form DPT in the second reaction stage.

Both stages of the present process can be carried out at temperatures within the range of about 20° to 100° C. The first stage of the process is preferably carried out between about 45° C. and 70° C., and the second stage of the reaction is preferably carried out at between about 20° C. and 30° C. The use of higher temperatures is not precluded but may result in increased side reactions and lower yields of DPT; the use of lower temperatures results in slower reaction rates and hence is less preferred.

The following example illustrates a specific embodiment of the method of carrying out the process of the present invention.

EXAMPLE 10.5 grams (0.1 mole) of nitrourea was mixed with 60 ml. (0.6 mole) of 37% aqueous formaldehyde. The mixture was warmed to 45° C. and agitated until the nitrourea was completely dissolved. The solution was cooled to about 25°-30° C. and adjusted to a pH of about 2-3 by addition of 5% aqueous sodium hydroxide. A vigorous evolution of carbon dioxide commenced, and the reaction mixture was stirred until $CO_2$ evolution ceased. The solution was then heated to 65° C. and stirred for about 1 hour, during which further $CO_2$ was liberated. The solution was cooled to room temperature and adjusted to a pH of 6-7 by addition of 43% ammonium hydroxide, whereupon DPT precipitated from solution and was separated by filtration. The filtrate was treated with more ammonium hydroxide, thus producing additional precipitate. The process was repeated until no further precipitate was obtained. The collected precipitates of DPT, when dried, weighed 5.8 grams, corresponding to a 52% of theory yield based on nitrourea. Analysis of DPT: Calculated: C, 27.5%; H, 4.63%; N, 38.5%. Found: C, 27.51%; H, 4.67%; N, 38.38%.

The foregoing disclosure is merely illustrative of the principles of this invention and is not to be interpreted in a limiting sense. I wish it to be understood that I do not desire to be limited to the exact details described because obvious modifications will occur to a person skilled in the art.

I claim:

1. A process for preparing 1,5-methylene-3,7-dinitro-1,3,5,7-tetraazacyclooctane (DPT) which comprises reacting nitrourea and formaldehyde in aqueous medium at a pH of about 2 to about 6-7 to cause the evolution of carbon dioxide gas and formation of an intermediate compound, and reacting the intermediate compound with aqueous ammonia and formaldehyde at a pH of about 6 to 7 to form DPT.

2. A process according to claim 1, wherein the reactions are carried out at a temperature within the range of 20° C. and 100° C.

3. A process according to claim 1, wherein the total amount of formaldehyde employed in the process is at least 2.5 moles per mole of nitrourea.

4. A process according to claim 1, wherein the reaction of nitrourea and formaldehyde is effected at a pH of between about 2 and 3.

5. A process according to claim 4, wherein the aqueous medium is adjusted to a pH between about 2 and 3 with sodium hydroxide.

6. A process according to claim 4 wherein the solution of pH between about 2-3 is heated to between 45° C. and 70° C.

* * * * *